US007012153B2

(12) United States Patent
Luke

(10) Patent No.: US 7,012,153 B2
(45) Date of Patent: Mar. 14, 2006

(54) PROCESS FOR PREPARING BENZOIC ACIDS

(75) Inventor: Wayne Douglas Luke, West Lafayette, IN (US)

(73) Assignee: Eli Lilly and Company, Indianapolis, IN (US)

( * ) Notice: Subject to any disclaimer, the term of this patent is extended or adjusted under 35 U.S.C. 154(b) by 7 days.

(21) Appl. No.: 10/745,188

(22) Filed: Dec. 22, 2003

(65) Prior Publication Data
US 2005/0137396 A1    Jun. 23, 2005

(51) Int. Cl.
*C07C 69/007* (2006.01)
*C07C 69/013* (2006.01)
*C07C 69/017* (2006.01)

(52) U.S. Cl. ...................................... 560/156; 560/227
(58) Field of Classification Search ................ 560/156, 560/227
See application file for complete search history.

(56) References Cited

U.S. PATENT DOCUMENTS

| 4,133,814 | A |   | 1/1979  | Jones et al. |         |
|-----------|---|---|---------|--------------|---------|
| 4,380,635 | A |   | 4/1983  | Peters       |         |
| 4,418,068 | A |   | 11/1983 | Jones        |         |
| 5,631,369 | A | * | 5/1997  | Kjell et al. | 540/610 |
| 5,750,688 | A | * | 5/1998  | Kjell et al. | 540/596 |
| 5,852,193 | A | * | 12/1998 | Chelius      | 546/238 |
| 6,075,146 | A | * | 6/2000  | Chelius      | 546/248 |

FOREIGN PATENT DOCUMENTS

| EP | 0 699 672    |   | 3/1996 |
| EP | 0699672 A1   | * | 6/1996 |

* cited by examiner

*Primary Examiner*—Elvis O. Price
(74) *Attorney, Agent, or Firm*—Gary M. Birch; Gilbert T. Voy; Francis O. Ginah

(57) ABSTRACT

An improved process for the preparation of 4[(2-piperidin-1-yl)ethoxy]benzoic acid derivatives, comprising reacting a haloalkyl amine of formula (III) with a compound of formula (IV) in the presence of a hydrated inorganic base in an appropriate solvent.

9 Claims, No Drawings

PROCESS FOR PREPARING BENZOIC ACIDS

FIELD OF THE INVENTION

The present invention relates to the fields of pharmaceutical and organic chemistry and provides a novel process for preparing 4[(2-piperidin-1-yl)ethoxy]benzoic acid derivative compounds.

BACKGROUND OF THE INVENTION

Compounds of formula I

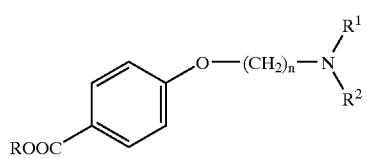

wherein;

R is $C_1$–$C_6$ alkyl;

$R^1$ and $R^2$ each are independently $C_1$–$C_4$ alkyl, or combine together with the nitrogen atom to which $R^1$ and $R^2$ n is 2 or 3; or acid salt thereof;

are important intermediates in the manufacture of compounds of formula II

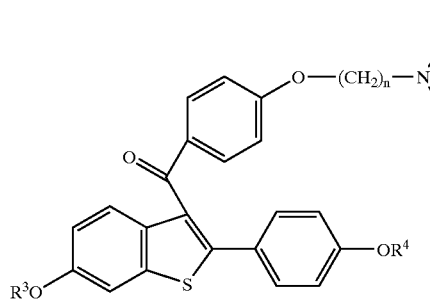

wherein;

$R^3$ and $R^4$ are independently hydrogen or a hydroxy protecting group; and $R^1$, $R^2$ and n are as defined above; or a pharmaceutically acceptable salt thereof.

Compounds of formula II, particularly raloxifene hydrochloride, in which $R^1$ and $R^2$ combine to form a piperidinyl moiety, $R^3$ and $R^4$ each are hydrogen, and n is 2, are well known in the pharmaceutical art as having activity for the treatment or prevention of certain disease states including, for example, osteoporosis.

Typically, compounds of formula I are prepared by reacting, for example, β-chloroethylpiperidine hydrochloride and ethyl 4-hydroxybenzoate in methyl ethyl ketone, in the presence of potassium carbonate (see, U.S. Pat. No. 4,418,068). An improved process for preparing compounds of formula I was disclosed in U.S. Pat. No. 5,631,369, the contents of which are incorporated herein by reference. The disclosures of both reference patents teach the use of anhydrous powdered potassium carbonate as the preferred base for enhancing the rate of the reaction, implying that the particle size of anhydrous potassium carbonate is crucial to the alkylation reaction.

Powdered potassium carbonate is relatively more expensive than granular hydrated potassium carbonate, and a controlled atmosphere may be required to maintain the anhydrous nature of powdered potassium carbonate. These factors add to the overall cost of manufacture of compounds of formula I and II.

Furthermore, the use of anhydrous potassium carbonate on a manufacturing scale results in a heterogenous mixture, thus limiting the ability to effectively agitate the mixture. This in turn makes it difficult to perform the reaction at a higher concentration, resulting ultimately in a lower throughput.

A more efficient, more robust and less costly process for preparing compounds of formula I and ultimately compounds of formula II is needed. Such a process would ideally obviate the use of powdered anhydrous potassium carbonate. Such a process would also result in a homogenous reaction mixture which increases reaction concentration and hence throughput. Such a process would be a significant and desirable advancement over the current state of the art. The present invention provides such a process.

SUMMARY OF THE INVENTION

The present invention provides a novel process for preparing compounds of formula I

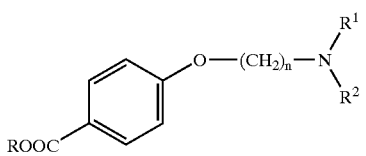

wherein;

R is $C_1$–$C_6$ alkyl;

$R^1$ and $R^2$ each are independently $C_1$–$C_4$ alkyl, or combine together with the nitrogen atom to which $R^1$ and $R^2$ are attached, to form piperidinyl, pyrrolidinyl, methylpyrrolidinyl, dimethylpyrrolidinyl, morpholino, or 1-hexamethyleneimino; and n is 2 or 3; or an acid salt thereof, which comprises:

reacting a haloalkyl amine of formula III

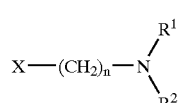

wherein;

X is a halogen; and $R^1$, $R^2$, and n are as defined above, with a compound of formula IV:

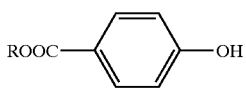

wherein R is $C_1$–$C_6$ alkyl, in the presence of a hydrated inorganic base, in an appropriate solvent.

The present invention further provides a process for preparing compounds of formula II

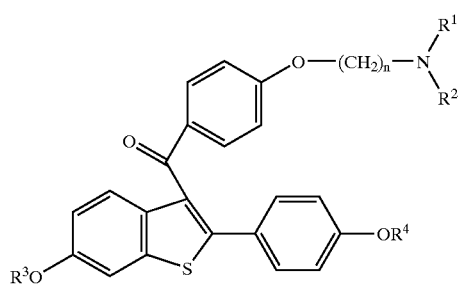

wherein;

$R^1$, $R^2$ and n, are as defined above and;

$R^3$ and $R^4$ are each independently hydrogen or a hydroxy protecting group; and n is 2 or 3;

or a pharmaceutically acceptable salt thereof, from compounds of formula I.

DETAILED DESCRIPTION OF THE INVENTION

General terms used in the description of chemical formulae herein bear their usual meanings. For example, the term "$C_1$–$C_4$ alkyl" refers to straight or branched chains of 1 to 4 carbon atoms including, methyl, ethyl, propyl, isopropyl, butyl, n-butyl, and isobutyl; and the term "$C_1$–$C_6$ alkyl" encompasses the groups included in the definition of "$C_1$–$C_4$ alkyl" in addition to groups such as pentyl, isopentyl, hexyl, isohexyl, and the like.

The term "halo" or "halogen" includes bromo, chloro, fluoro, and iodo.

The term "appropriate solvent" as used herein refers to a $C_1$–$C_6$ alkyl acetate possessing the desired boiling point for the particular reaction substrate, and possessing an appropriate miscibility with an aqueous phase for the substrate of the reaction.

The terms "appropriate aqueous acid" or "appropriate acid" as used herein refer to any one of the inorganic or organic acids capable of protonating a basic group such as an amino group or a carboxylate anion to form the corresponding acid addition salt or acid, without effecting deleterious manipulations of the molecule.

Examples include but are not limited to aqueous hydrochloric acid, anhydrous hydrogen chloride, dilute phosphoric acid, dilute sulfuric acid, acetic acid and the like.

The term "acid salt" as used herein denote non-covalently bonded, addition compounds formed by the reaction of an organic or inorganic acid which is water soluble, preferably an inorganic acid with a basic molecule i.e., a molecule containing typically an amino group or other nitrogen atom containing group, for example, a compound of formula I.

The term "hydrated inorganic base" as used herein refers to non-anhydrous inorganic base, for example, sodium carbonate containing from 1 to 20% water of hydration or up to the limit of hydration for the particular base. The water content (hence the hydration) can be attained by (1) addition of water as a bulk solvent or (2) introduced with potassium carbonate as water of hydration of the potassium carbonate. Hydrated potassium carbonate can be obtained commercially as potassium carbonate sesquihydrate.

The terms "hydroxy protecting group" and "—OH protecting group" as used herein are synonymous, and bear the commonly understood meaning and refer particularly, to a group used to replace the hydrogen atom of a hydroxy group for the purposes of avoiding reaction at the hydroxy group, providing bulk or other generally understood purposes.

In formula II compounds, the $R^3$ and $R^4$ hydroxy protecting groups, when $R^3$ and $R^4$ are not hydrogen, denote groups which generally are not found in the final therapeutically active compounds, but which are intentionally introduced during a portion of the synthetic process to protect a group which otherwise might react in the course of chemical manipulations, and is then removed at a later stage of the synthesis. Since compounds bearing such protecting groups are of importance primarily as chemical intermediates (although some derivatives also exhibit biological activity), their precise structure is not critical. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley (New York, 1981); and *The Peptides*, Vol. I, Schrooder and Lubke, Academic Press (London and New York, 1965). Representative hydroxy protecting groups include, for example, —$C_1$–$C_4$ alkyl, —CO—($C_1$–$C_6$ alkyl), —$SO_2$—($C_4$–$C_6$ alkyl), and —CO—Ar in which Ar is optionally substituted phenyl.

The term "substituted phenyl" refers to a phenyl group having one or more substituents selected from the group consisting of $C_1$–$C_4$ alkyl, $C_1$–$C_5$ alkoxy, hydroxy, nitro, chloro, fluoro, and tri(chloro or fluoro) methyl. The term "$C_1$–$C_5$ alkoxy" represents a $C_1$–$C_5$ alkyl group attached through an oxygen bridge such as, for example, methoxy, ethoxy, n-propoxy, isopropoxy, and the like. Preferred $R^3$ and $R^4$ hydroxy protecting groups are $C_1$–$C_4$ alkyl, particularly methyl.

The present invention provides a process for preparing a compound of formula I which is illustrated in Scheme 1 below:

Scheme 1

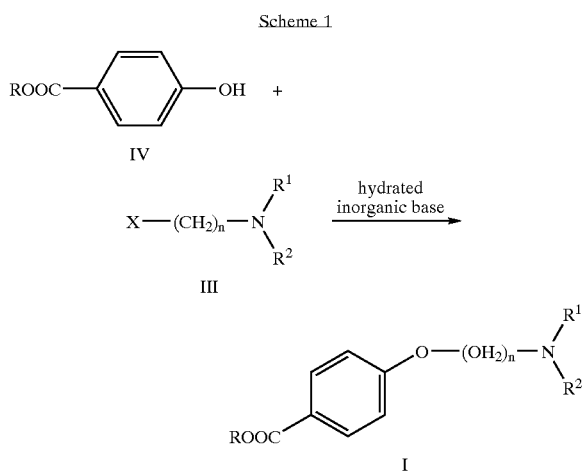

where X, $R^1$, $R^1$ and $R^2$ are defined above.

In the present novel process, an amount of a haloalkyl amine of formula III is reacted with about 1 mole equivalent of a 4-hydroxybenzoate of formula IV and a hydrated inorganic base, in the presence of an appropriate solvent. Typically from about 1 to 3 molar equivalents, preferably from about 1 to 1.5 molar equivalents and most preferably about 1.05 molar equivalent of haloalkyl amine of formula III is utilized. Similarly from about 1 to 3 molar equivalents, preferably from about 1 to 1.5 molar equivalents and most preferably 1.05 molar equivalent of base is utilized. A preferred formula III compound is that in which $R^1$ and $R^2$ combine to form piperidinyl, n is 2, and X is chloro, while a preferred formula IV compound is that in which R is methyl.

A preferred solvent is a $C_1$–$C_6$ alkyl acetate solvent including those in which the alkyl moiety of such solvent is a straight or branched chain alkyl moiety having one to six carbon atoms. Preferred alkyl acetate solvents include, for example, ethyl acetate, propyl acetate, isopropyl acetate, butyl acetate, amyl acetate, isoamyl acetate, and the like. A most preferred $C_1$–$C_6$ alkyl acetate solvent is amyl acetate.

In addition to an alkyl acetate solvent, the present process, as well as the processes described below, is run in the presence of an appropriate hydrated inorganic base. A hydrated inorganic base such as a carbonate or bicarbonate base, is preferred. Of these, granular potassium carbonate containing from about 1–20% of water is preferred. Granular potassium carbonate with from about 3–5% water content is the most efficient for enhancing the rate of completion of the reaction and hence is most preferred for the practice of the invention.

Furthermore, it is preferred to maintain the alkylation reaction mixture under an inert atmosphere, such as, for example, argon, or, particularly, nitrogen.

The present reaction may be run at a temperature from about 80° C. to the reflux temperature of the solvent. A preferred temperature range is from about 100° C. to about 150° C., while a range from about 118° C. to about 125° C. is especially preferred.

The length of time for this reaction is that amount necessary for the reaction to substantially occur. Typically, this reaction takes from about 2 to 24 hours. The optimal time can be determined by monitoring the progress of the reaction via conventional chromatographic techniques. A preferred reaction time is from 2 to 6 hours. A particularly preferred reaction time is from 4.5 to 5.5 hours. A most preferred reaction time is from 4 to 4.5 hours.

Upon completion of this reaction, the alkylation mixture is cooled, to between about 30° C. and about 70° C., and washed with water to dissolve the added basic salt. An appropriate aqueous acid is then added to the mixture to extract the compound of formula I.

Preferably, aqueous hydrochloric acid is used for the extraction process, forming a hydrochloride salt of the formula I compound. Other aqueous acids such as, for example, sulfuric acid, phosphoric acid, acetic acid and the like, may be used, and the corresponding formula I acid salt is provided. One of skill in the art is aware that the compound of formula I may optionally be isolated as the free base by methods known in the art including but not limited to chromatography, distillation and or crystallization. Preferably, the acid salt of the formula I compound may be utilized in- situ without isolation.

Optionally, the aryl or alkyl ester of the desired formula I compound is cleaved via standard procedures, providing a compound of formula Ia

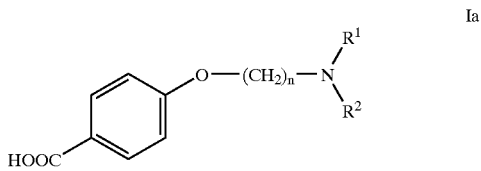

wherein;
R1, R2, and n are as defined above.

Typically, the formula I acid compound is heated to a temperature in the range from about 80° C. to about 150° C., preferably from about 95° C. to about 100° C. At the preferred temperature range, an acceptable level of formula Ia compound is produced in about 4 hours. Continued heating for up to 24 hours will not affect either quality or yield. Optionally, while applying heat in the above-stated temperature range, the ester cleaving may be accelerated by distilling and removing the alcohol formed via acid hydrolysis.

Isolation and purification of the acid compound, formula Ia, is accomplished using procedures well known to one of ordinary skill in the art (See also U.S. Pat. No. 5,631,369). Generally, the resulting mixture from the ester cleavage step is cooled to a temperature range from about −5° C. to about 20° C. Although the product will crystallize or precipitate out of solution at this range, the optimum temperature range is from about 0° C. to about 5° C. The desired formula Ia compound is then isolated by filtration or other techniques known to practitioners of the art.

Compounds of formula I or derivatives thereof, can be converted to the compounds of formula II as illustrated in scheme 2 below:

Scheme 2

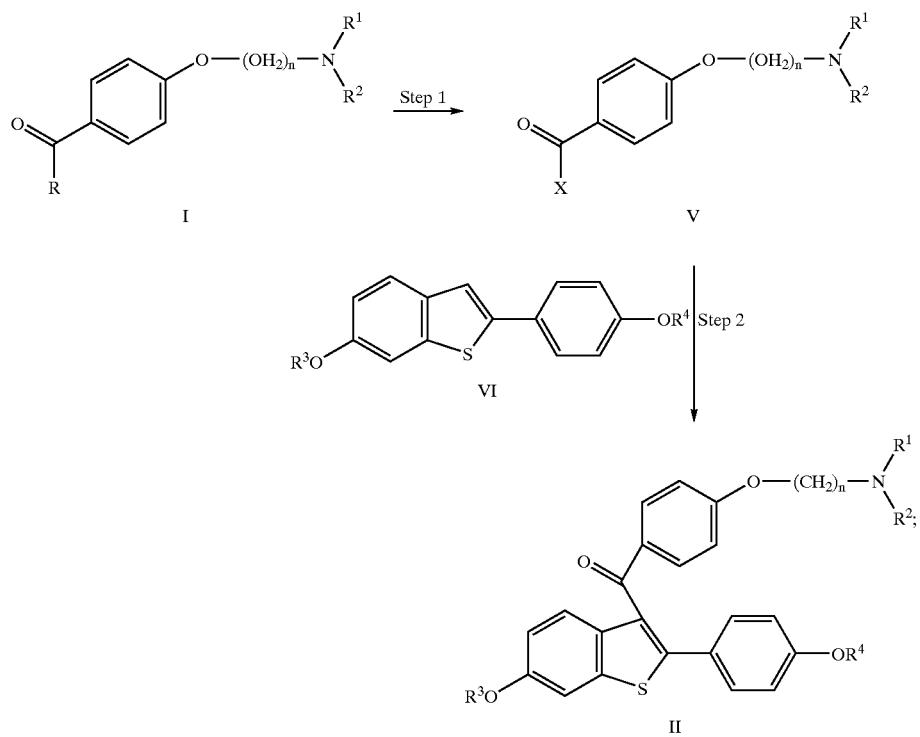

wherein X is a halogen, preferably bromine or chlorine; and R, R¹, R², R³, and R⁴ are as defined above.

In general, a compound of formula I or its derivative such as the amide, formyl or acid derivates are converted to the acid halide compound of formula V, preferably an acid chloride or acid bromide, by methods well known to one skilled in the art. General reference texts for the formation of acid chlorides (acyl halides) include for example, March, J. *Advanced Organic Chemistry*, John Wiley and Sons, New York, N.Y., 1985, and Larock, R. C. *Comprehensive organic transformations*, (1989), VCH Publishers Inc. New York, N.Y. A preferred procedure for acyl halide formation (step 1) involves reacting the acid compound Ia, with an acyl halide forming reagent to provide a compound of formula V, in a solvent such as dichloromethane, 1,2-dichloroethane, toluene or tetrahydrofuran. Typical acyl halide forming reagents include but are not limited to phospgene, thionyl chloride, oxalyl chloride, phosphorus trichloride, triphenylphosphine dibromide and acids such as hydrochloric, and hydrogen fluoride. Preferred acyl halide forming agents for the practice of this invention include oxalyl chloride, anhydrous hydrogen chloride, thionyl chloride. Most preferred is thionyl chloride.

In step 2, the acyl halide compound of formula V may be acylated with a compound of formula VI to provide a compound of formula II. Compounds of formula VI and procedures for the acylation step are known in the art and are also described for example, by Peters in U.S. Pat. No. 4,380,635, and in Jones, et al., in U.S. Pat. Nos. 4,133,814 and 4,418,068, each of which is herein incorporated by reference. A preferred formula I compound for the present acylation reaction is that in which R¹ and R² are combined together with the nitrogen atom to which R¹ and R² are attached, to form piperidinyl and n is 2.

One skilled in the art is aware that particular steps of the process of this invention may be inverted or omitted without adverse effect on the practice of the invention. Furthermore certain steps such as formation of pharmaceutically acceptable salts, deprotection and/or exchange of protecting groups may be performed at different points and such acts may be advantageous depending on the particular starting material or derivatives thereof employed.

Reagents and all parameters necessary to carry out the acylation, the optional deprotection, an optional salt formation step within scheme 2, and isolation and purification of formula II compounds are described in the afore-incorporated United States patents. Thus, pharmaceutically active compounds of formula II, including their acid addition salts, are prepared via the instant process of the present invention.

EXAMPLES

The following examples are provided for the purpose of illustrating the present invention and are not intended to be limiting upon the scope of the invention.

Example 1

Preparation of 4-(2-piperidinoethoxy)benzoic acid hydrochloride

To a 2000 gallon reaction tank were added: 1320L of amyl acetate, 167.42 kg of methyl 4-hydroxybenzoate, 408.6 kg of anhydrous potassium carbonate, and 283.5 kg of β-chloroethylpiperidine hydrochloride. The mixture was heated to 120° C.–125° C. for 5 hours, at which time HPLC analysis indicated complete consumption of the methyl 4-hydroxybenzoate. The tank was cooled to less than 50° C. 880L of deionized water were added to the tank. The layers were separated and the aqueous layer was discarded. In a glass-lined tank was mixed 367 liters of food grade hydrochloric acid and 184L of deionized water. The acid mixture was combined with the organic layer. The layers were separated and the organic layer was discarded. The mixture of the intermediate ester in aqueous acid heated to reflux until HPLC suggested no further consumption of the ester (13 hours). The mixture was cooled to less than 40° C., 550 liters of acetone was added to the mixture and the mixture was cooled to 0° C.–5° C. and stirred for 1 hour. The product was collected by filtration on a centrifuge. The wet cake was rinsed on the centrifuge with 400L of acetone. The product was dried in a rotary vacuum (double cone) dryer at less than 50° C. and 25–27 inches in mercury. Yield was 91% of theoretical.

Example 2

Preparation of 4-(2-piperidinoethoxy)benzoic acid hydrochloride

A 17.57 g portion of methyl 4-hydroxybenzoate and 132 mL of amyl acetate were combined. To this slurry at ambient temperature, was added 29.19 g of potassium carbonate sesquihydrate (particle size 96% greater than 100 mesh, 100% greater than 200 mesh) and 20.26 g of β-chloroethylpiperidine hydrochloride. The mixture was heated to 110° C.–115° C. for 4.5 hours. The solution was cooled to less than 50° C. and 88 ml of deionized water were added. The layers were separated and the aqueous layer was discarded. To the organic phase was added 88 mL of deionized water the biphasic mixture stirred for 15 minutes and the phases separated. The aqueous phase was discarded. A dilute solution of aqueous hydrochloride acid was prepared by adding 42.6 g of reagent grade hydrochloric acid to 15 mL of deionized water. This solution was added to the organic phase, stirred for 15 minutes and the phases separated. The organic phase was discarded. The aqueous phase was heated to reflux for 5 hours. After approximately 1.5 hours at reflux the desired product began to precipitate. The product slurry was cooled to less than 40° C. and 55 mL of acetone was added. The mixture was cooled to 0° C.–5° C. and stirred for 1 hour. The product was collected by filtration and washed with a minimum of acetone pre-chilled to 0° C. The product was dried in a vacuum oven at ambient temperature. Yield was 90.6% of theory. The potency of the product by HPLC compared to a reference standard was 99.2%.

Example 3

Preparation of 4-(2-piperidinoethoxy)benzoic acid hydrochloride

A 17.57 g portion of methyl 4-hydroxybenzoate and 132 mL of amyl acetate were combined. To this slurry at ambient temperature, was added 29.19 g of powdered potassium carbonate (11% water by Karl Fischer particle size not less than 95% passing a 100 mesh sieve and not less than 90% passing a 200 mesh sieve) and 20.26 g of β-chloroethylpiperidine hydrochloride. The mixture was heated to 110° C.–115° C. for 4.5 hours. The solution was cooled to less than 50° C. and 88 mL of deionized water were added. The layers were separated and the aqueous layer was discarded. To the organic phase was added 88 mL of deionized water the biphasic mixture stirred for 15 minutes and the phases separated. The aqueous phase was discarded. A dilute solution of aqueous hydrochloride acid was prepared by adding 42.6 g of reagent grade hydrochloric acid to 15 mL of deionized water. This solution was added to the organic phase, stirred for 15 minutes and the phases separated. The organic phase was discarded. The aqueous phase was heated to reflux for 5 hours. After approximately 1.5 hours at reflux the desired product began to precipitate. The product slurry was cooled to less than 40° C. and 55 mL of acetone was added. The mixture was cooled to 0° C.–5° C. and stirred for 1 hour. The product was collected by filtration and washed with a minimum of acetone pre-chilled to 0° C. The product was dried in a vacuum oven at ambient temperature. Yield was 93.4% of theory. The potency of the product by HPLC calibrated against a reference standard was 101.0%.

Example 4

Preparation of 4-(2-piperidinoethoxy)benzoic acid hydrochloride

A 17.57 g portion of methyl 4-hydroxybenzoate and 132 mL of amyl acetate were combined. To this slurry at ambient temperature, was added 29.19 g of powdered potassium carbonate (11% water by Karl Fischer particle size not less than 95% passing a 100 mesh sieve and not less than 90% passing a 200 mesh sieve), 4.78 g of deionized water and 20.26 g of β-chloroethylpiperidine hydrochloride. The mixture was heated to 118° C.–125° C. for 4.5 hours. The solution was cooled to less than 50° C. and 88 mL of deionized water were added. The layers were separated and the aqueous layer was discarded. To the organic phase was added 88 mL of deionized water the biphasic mixture stirred for 15 minutes and the phases separated. The aqueous phase was discarded. A dilute solution of aqueous hydrochloride acid was prepared by adding 42.6 g of reagent grade hydrochloric acid to 15 mL of deionized water. This solution was added to the organic phase, stirred for 15 min and the phases separated. The organic phase was discarded. The aqueous phase was heated to reflux for 5 hours. After approximately 1.5 hours at reflux the desired product began to precipitate. The product slurry was cooled to less than 40° C. and 55 mL of acetone was added. The mixture was cooled to 0° C.–5° C. and stirred for 1 hour. The product was collected by filtration and washed with a minimum of acetone pre-chilled to 0° C. The product was dried in a vacuum oven at ambient temperature. Yield was 91.3% of theory. The potency of the product by HPLC calibrated against a reference standard was 101.0%.

Example 5

Preparation of 4-(2-piperidinoethoxy)benzoic acid hydrochloride

A 50.22 g portion of methyl 4-hydroxybenzoate and 198 mL of amyl acetate were combined. To this slurry at ambient temperature, was added 122.58 g of powdered potassium carbonate (0.8% water by Karl Fischer particle size not less than 95% passing a 100 mesh sieve and not less than 90% passing a 200 mesh sieve), 19.61 g of deionized water and 85.04 g of β-chloroethylpiperidine hydrochloride. The mixture was heated to 118° C.–125° C. for 4.5 hours. The solution was cooled to less than 50° C. and 132 mL of deionized water were added. The layers were separated and the aqueous layer was discarded. To the organic phase was added 132 mL of deionized water the biphasic mixture stirred for 15 minutes and the phases separated. The aqueous phase was discarded. A dilute solution of aqueous hydrochloride acid was prepared by adding 127.8 g of reagent grade hydrochloric acid to 45 mL of deionized water. This solution was added to the organic phase, stirred for 15 minutes and the phases separated. The organic phase was discarded. The aqueous phase was heated to reflux for 5 hours. After approximately 1.5 hours at reflux the desired product began to precipitate. The product slurry was cooled to less than 40° C. and 123.7 mL of acetone was added. The mixture was cooled to 0° C.–5° C. and stirred for 1 hour. The product was collected by filtration and washed with a minimum of acetone pre-chilled to 0° C. The product was dried in a vacuum oven at ambient temperature. Yield was 93.7% of theory. The potency of the product by HPLC vs a reference standard was 100.0%.

Example 6

Preparation of 4-(2-piperidinoethoxy)benzoic acid hydrochloride

A 37.66 g portion of methyl 4-hydroxybenzoate and 198 mL of amyl acetate were combined. To this slurry at ambient temperature, was added 91.93 g of powdered potassium carbonate (0.8% water by Karl Fischer particle size not less than 95% passing a 100 mesh sieve and not less than 90% passing a 200 mesh sieve), 14.7 g of deionized water and 63.78 g of β-chloroethylpiperidine hydrochloride. The mixture was heated to 118° C.–125° C. for 4.5 hours. The solution was cooled to less than 50° C. and 132 mL of deionized water were added. The layers were separated and the aqueous layer was discarded. To the organic phase was added 132 mL of deionized water the biphasic mixture stirred for 15 minutes and the phases separated. The aqueous phase was discarded. A dilute solution of aqueous hydrochloride acid was prepared by adding 95.85 g of reagent grade hydrochloric acid to 33.75 mL of deionized water. This solution was added to the organic phase, stirred for 15 minutes and the phases separated. The organic phase was discarded. The aqueous phase was heated to reflux for 5 hours. After approximately 1.5 hours at reflux the desired product began to precipitate. The product slurry was cooled to less than 40° C. and 123.7 mL of acetone was added. The mixture was cooled to 0° C.–5° C. and stirred for 1 hour. The product was collected by filtration and washed with a minimum of acetone pre-chilled to 0° C. The product was dried in a vacuum oven at ambient temperature. Yield was 93.2% of theory. The potency of the product by HPLC versus a reference standard was 100.5%.

Example 7

Preparation of 4-(2-piperidinoethoxy)benzoic acid hydrochloride

A 50.22 g portion of methyl 4-hydroxybenzoate and 198 mL of amyl acetate were combined. To this slurry at ambient temperature was added 122.58 g of powdered potassium sesquihydrate and 85.04 g of β-chloroethylpiperidine hydrochloride. The mixture was heated to 118° C.–125° C. for 4.5 hours. The solution was cooled to less than 50° C. and 132 mL of deionized water were added. The layers were separated and the aqueous layer was discarded. To the organic phase was added 132 mL of deionized water the biphasic mixture stirred for 15 minutes and the phases separated. The aqueous phase was discarded. A dilute solution of aqueous hydrochloride acid was prepared by adding 63.9 g of reagent grade hydrochloric acid to 45 mL of deionized water. This solution was added to the organic phase, stirred for 15 minutes and the phases separated. The organic phase was discarded. The aqueous phase was heated to reflux for 5 hours. After approximately 1.5 hours at reflux the desired product began to precipitate. The product slurry was cooled to less than 40° C. and 123.7 mL of acetone was added. The mixture was cooled to 0° C.–5° C. and stirred for 1 hour. The product was collected by filtration and washed with a minimum of acetone pre-chilled to 0° C. The product was dried in a vacuum oven at ambient temperature. Yield was 94.7% of theory. The potency of the product by HPLC versus a reference standard was 99.2%.

Example 8

Preparation of 4-(2-piperidinoethoxy)benzoic acid hydrochloride Effect of Water Content and Potassium Particle Size on Reaction A 25.11 g portion of methyl 4-hydroxybenzoate and 198 mL of amyl acetate were combined. To this slurry at ambient temperature, was added 61.29 g of powdered potassium carbonate (0.8% water by Karl Fischer particle size not less than 95% passing a 100 mesh sieve and not less than 90% passing a 200 mesh sieve) and 42.52 g of β-chloroethylpiperidine hydrochloride. The mixture was heated to 118° C.–125° C. for 4.5 hours at which time HPLC analysis indicated complete consumption of the methyl 4-hydroxybenzoate. The solution was cooled to less than 50° C. and 132 mL of deionized water were added. The layers were separated and the aqueous layer was discarded. To the organic phase was added 132 mL of deionized water the biphasic mixture stirred for 15 minutes and the phases separated. The aqueous phase was discarded. A dilute solution of aqueous hydrochloride acid was prepared by adding 63.9 g of reagent grade hydrochloric acid to 22.5 mL of deionized water. This solution was added to the organic phase, stirred for 15 min and the phases separated. The organic phase was discarded. The aqueous phase was heated to reflux for 5 hours. After approximately 1.5 hours at reflux the desired product began to precipitate. The product slurry was cooled to less than 40° C. and 123.7 mL of acetone was added. The mixture was cooled to 0° C.–5° C. and stirred for 1 hour. The product was collected by filtration and washed with a minimum of acetone pre-chilled to 0° C. The product was dried in a vacuum oven at ambient temperature. Yield was 90.8% of theory. The potency of the product by HPLC versus a reference standard was 100.0%.

Example 9

Preparation of 4-(2-piperidinoethoxy)benzoic acid hydrochloride

The procedure of Example 8 was followed except that the particle size of the anhydrous potassium carbonate was as follows 94.4% passing a 10 mesh sieve, 88.8% passing a 20 mesh sieve, 77.4% passing a 40 and 160 mesh sieve and no material passing a 325 mesh sieve. After the initial reaction period of 4.5 hours at 118° C.–125° C. less than 15% of the methyl 4-hydroxybenzoate had been converted to methyl 4-(2-piperidinoethoxy) benzoate.

Example 10

Preparation of 4-(2-piperidinoethoxy)benzoic acid hydrochlorid

The procedure of Example 8 except that 1.84 g of deionized water (3% by weight of the potassium carbonate charged) was added immediately after the potassium carbonate charge. After the initial reaction period of 4.5 hours at 118° C.–125° C. HPLC analysis indicated complete consumption of the methyl 4-hydroxybenzoate. Yield was 91.6% of theory. The potency of the product by HPLC versus a reference standard was 99.3%.

Example 11

Preparation of 4-(2-piperidinoethoxy)benzoic acid hydrochloride

The procedure of Example 8 except that 9.8 g of deionized water (16% by weight of the potassium carbonate charged) was added immediately after the potassium carbonate charge. After the initial reaction period of 4.5 hours at 118° C.–125° C. HPLC analysis indicated complete consumption of the methyl 4-hydroxybenzoate. Yield was 91.9% of theory. The potency of the product by HPLC versus a reference standard was 98.5%.

Example 12

Preparation of 6-methoxy-2-(4-methoxyphenyl)benzo[b]thiophene

A 100 g portion of 3-methoxybenzenethiol and 39.1 g of potassium hydroxide dissolved in 300 mL of water were added to 750 mL of denatured ethanol, and the flask was put in a cooling bath. A total of 164 g of α-bromo-1-methoxyacetophenone was then added in small portions, and the mixture was stirred for 10 minutes in the cooling bath after the addition was complete and then for 3 hours at ambient temperature. The solvent was then evaporated off in vacuum, and 200 mL of water was added. The mixture was extracted with ethyl acetate, and the organic layer was washed twice with water, twice with aqueous sodium bicarbonate solution and twice with aqueous sodium chloride solution. The organic layer was then dried over magnesium sulfate, filtered and evaporated under vacuum to obtain 202 g of crude a-(3-methoxyphenylthio)-4-methoxyacetophenone, which was recrystallized with hexane to obtain 158 g of preferred product, mp. 53° C.

A 124 g portion of the above intermediate was added in small portions to 930 g of polyphosphoric acid at 85° C. The temperature rose to 95° C., during the addition, and the mixture was stirred at 90° C. for 30 minutes after the addition was complete, and was then stirred an additional 45 minutes while it cooled without external heating. One liter of crushed ice was then added to the mixture, and the external ice bath was applied to control the temperature while the ice melted and diluted the acid. 500 mL of additional water was added, and the light pink precipitate was filtered off and washed, first with water and then with methanol. The solids were dried under vacuum at 40° C. to obtain 119 g of crude 6-methoxy-2-(4-methoxyphenyl)benzo[b]thiophene. The crude product was slurried in hot methanol, filtered, and washed with cold methanol, and the solids were recrystallized from 4 liters of ethyl acetate, filtered, washed with hexane and dried to obtain 68 g of the desired intermediate product, m.p. 187° C.–190.5° C.

Example 13

Preparation of Raloxifene Hydrochloride [6-hydroxy-2-(4-hydroxyphenyl)-3-[4-(2-piperidinoethoxy)benzyl]benzo[b]thiophene hydrochloride]

Under a nitrogen blanket, a mixture of 3 g of 4-(2-piperidinoethoxy)benzoic acid, hydrochloride, 2 drops of dimethylformamide, 2.5 mL of thionyl chloride and 40 mL of chlorobenzene was heated at 70° C.–75° C. for about 1 hour. The excess thionyl chloride and 15–20 mL solvent were then distilled off. The remaining suspension was cooled to ambient temperature and to it were added 100 mL of dichloromethane, 2.7 g of 6-methoxy-2-(4-methoxyphenyl)benzo[b]thiophene (preparation of which is described in Example 14) and 10 g of aluminum chloride. After the solution was stirred for about 1 hour, 7.5 mL of ethanethiol was added, and the mixture was stirred for an additional 45 minutes. Then 40 mL of tetrahydrofuran was added, followed by 15 mL of 20% hydrochloric acid, with an exotherm to reflux. 50 mL of water and 25 mL of saturated aqueous sodium chloride were added. The mixture was stirred and allowed to cool to ambient temperature. The precipitate was collected by filtration and washed successively with 30 mL of water, 40 mL of 25% aqueous tetrahydrofuran and 35 mL of water. The solids were then dried at 40° C. under vacuum to obtain 5.05 g of product, which was identified by nuclear magnetic resonance as (6-hydroxy-2-(4-hydroxyphenyl)-3-[4-(2-peridinoethoxy)benzyl]benzo[b]thiophene hydrochloride).

I claim:
1. A process for preparing a compound of formula I

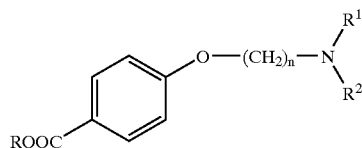

wherein;

R is $C_1$–$C_6$ alkyl;

$R^1$ and $R^2$ each are independently $C_1$–$C_4$ alkyl, or combine together with the nitrogen atom to which $R^1$ and $R^2$ are attached, to form piperidinyl, pyrrolidinyl, methylpyrrolidinyl, dimethylpyrrolidinyl, morpholino, or 1-hexamethyleneimino; and n is 2 or 3;

or a pharmaceutically acceptable salt thereof, which comprises the step of:

reacting a haloalkyl amine of formula III

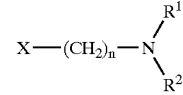

wherein;

X is a halogen; and $R^1$, $R^2$, and n are as defined above, with a compound of formula IV

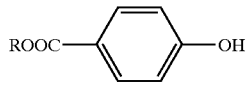

wherein;

R is $C_1$–$C_6$ alkyl, in the presence of a base hydrated with 1–20% water and an appropriate solvent wherein said base is selected from the group consisting of potassium carbonate, sodium hydroxide, potassium hydroxide, lithium hydroxide, sodium carbonate and calcium carbonate.

2. The process according to claim 1 further comprising the steps of:
  a) extracting the reaction product of claim 1 with an aqueous acid; and optionally
  b) cleaving the ester of the reaction product from step a) to form an acid compound of formula Ia

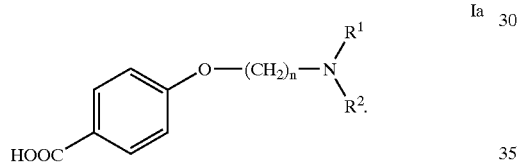

3. The process according to claim 1 wherein the solvent is a $C_1$–$C_6$ alkyl acetate solvent selected from the group consisting of amyl acetate, isopropyl acetate, isobutyl acetate and ethyl acetate.

4. The process according to claim 3 wherein the solvent is amyl acetate.

5. The process according to claim 1 wherein said hydrated base is potassium carbonate sesquihydrate.

6. The process according to claim 1 wherein $R^1$ and $R^2$ combine together with the nitrogen atom to which $R^1$ and $R^2$ are attached to form piperidinyl; and n is 2.

7. The process according to claim 2 wherein said aqueous acid is hydrochloric acid.

8. A process for preparing a compound of formula II

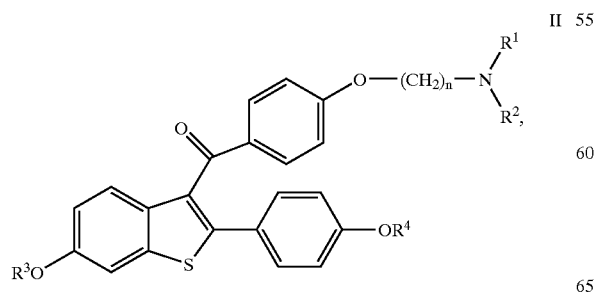

or a pharmaceutically acceptable salt thereof, wherein:

$R^1$ and $R^2$ each are independently $C_1$–$C_4$ alkyl, or combine together with the nitrogen atom to which $R^1$ and $R^2$ are attached, to form piperidinyl, pyrrolidinyl, methylpyrrolidinyl, dimethylpyrrolidinyl, morpholino, or 1-hexamethyleneimino; and n is 2 or 3;

$R^3$ and $R^4$ are independently hydrogen or a hydroxy protecting group;

comprising the steps of:

a) reacting a haloalkyl amine of formula III

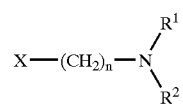

wherein;

X is a halogen; and $R^1$, $R^2$, and n are as defined above, with a compound of formula IV

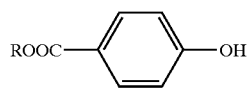

wherein;

R is $C_1$–$C_6$ alkyl;

in the presence of a base hydrated with 1–20% water and an appropriate solvent wherein said base is selected from the group consisting of potassium carbonate, sodium hydroxide, potassium hydroxide, lithium hydroxide, sodium carbonate, and calcium carbonate;

to form a compound of formula I

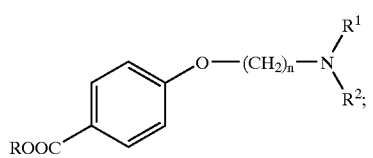

b) cleaving the ester of the reaction product from step a) to form an acid compound of formula Ia

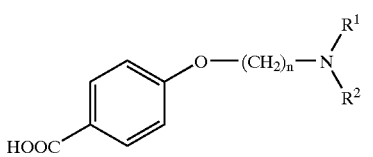

c) reacting a compound of formula Ia with an acyl halide forming agent to form a compound of formula V

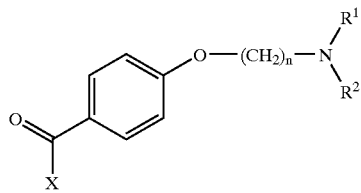

V wherein X is a halogen, and d) reacting a compound of formula V with a compound of formula VI

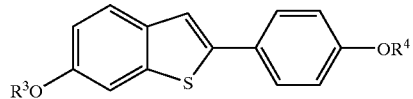

VI wherein $R^3$ and $R^4$ are as defined above, or a pharmaceutically acceptable salt thereof.

9. The process according to claim 8 wherein;

$R^1$ and $R^2$ combine with the nitrogen atom to which $R^1$ and $R^2$ are attached to form a piperidinyl moiety, $R^3$ and $R^4$ each are hydrogen, and n is 2.

* * * * *